United States Patent
Engelhart et al.

(10) Patent No.: US 7,323,072 B2
(45) Date of Patent: Jan. 29, 2008

(54) MULTI-ROLL BONDING AND APERTURING

(75) Inventors: Darin Allen Engelhart, Appleton, WI (US); James Alvin Boldra, Menasha, WI (US); Robert John Leveille, Appleton, WI (US); Robert Eugene Vogt, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 492 days.

(21) Appl. No.: 11/117,558

(22) Filed: Apr. 27, 2005

(65) Prior Publication Data

US 2006/0243367 A1    Nov. 2, 2006

(51) Int. Cl.
*B32B 37/00*    (2006.01)

(52) U.S. Cl. .................... 156/73.2; 156/73.3; 156/252; 156/253

(58) Field of Classification Search ............... 156/62.2, 156/62.6, 62.8, 73.1, 73.2, 73.3, 250, 252, 156/253, 308.2, 308.4
See application file for complete search history.

(56) References Cited

U.S. PATENT DOCUMENTS

| | | | |
|---|---|---|---|
| 3,542,634 A | 11/1970 | Such et al. | |
| 4,272,473 A | 6/1981 | Riemersma et al. | |
| 4,276,336 A | 6/1981 | Sabee | |
| 4,280,978 A | 7/1981 | Dannheim et al. | |
| 4,614,679 A | 9/1986 | Farrington, Jr. et al. | |
| 4,886,632 A | 12/1989 | Van Iten et al. | |
| 4,919,738 A | 4/1990 | Ball et al. | |
| 5,522,810 A | 6/1996 | Allen, Jr. et al. | |
| 5,562,650 A | 10/1996 | Everett et al. | |
| 5,599,338 A | 2/1997 | Enloe | |
| 5,667,619 A | 9/1997 | Alikhan | |
| 5,727,458 A | 3/1998 | Schulz | |
| 5,735,984 A * | 4/1998 | Hoff et al. | 156/73.3 |
| 5,833,679 A | 11/1998 | Wada | |
| 5,879,494 A * | 3/1999 | Hoff et al. | 156/73.3 |
| 6,248,195 B1 | 6/2001 | Schmitz | |
| 6,277,224 B1 * | 8/2001 | Muesch et al. | 156/73.3 |
| 6,452,064 B1 | 9/2002 | Thoren et al. | |
| 6,534,149 B1 | 3/2003 | Daley et al. | |
| 6,551,436 B1 | 4/2003 | Flohr et al. | |
| 6,733,605 B1 | 5/2004 | Lamping et al. | |
| 6,739,024 B1 | 5/2004 | Wagner | |

(Continued)

FOREIGN PATENT DOCUMENTS

DE    101 32 196 A1    1/2003

(Continued)

*Primary Examiner*—James Sells
(74) *Attorney, Agent, or Firm*—David J. Arteman

(57) ABSTRACT

A method and apparatus for bonding and aperturing one or more fibrous webs including bonding at least one fibrous web in a bonding nip created by a rotatable bonding roll and a rotatable anvil roll and aperturing the at least one fibrous web in an aperturing nip created by a rotatable aperture roll and an anvil roll. The bonding roll has a plurality of protuberances extending from the peripheral bonding surface that define a bonding pattern and result in highly bonded regions within the fibrous web. The aperture roll has a plurality of projections extending from the peripheral aperture surface that define an aperturing pattern. The aperturing pattern substantially aligns with the bonding pattern thereby creating apertures within the highly bonded regions.

15 Claims, 10 Drawing Sheets

U.S. PATENT DOCUMENTS

| | | |
|---|---|---|
| 6,830,800 B2 | 12/2004 | Curro et al. |
| 2003/0003269 A1 | 1/2003 | Lee et al. |
| 2003/0121380 A1 | 7/2003 | Cowell et al. |
| 2004/0163783 A1 | 8/2004 | Muller |

FOREIGN PATENT DOCUMENTS

| | | |
|---|---|---|
| EP | 0 000 387 A1 | 1/1979 |
| EP | 0 959 842 B1 | 7/2001 |
| WO | WO 94/20054 A1 | 9/1994 |
| WO | WO 97/11662 A1 | 4/1997 |
| WO | WO 00/13636 A1 | 3/2000 |
| WO | WO 01/45616 A1 | 6/2001 |
| WO | WO 02/31245 A2 | 4/2002 |
| WO | WO 2004/007157 A1 | 1/2004 |

* cited by examiner

MULTI-ROLL BONDING AND APERTURING

BACKGROUND OF THE INVENTION

This invention generally relates to fibrous webs and fibrous web laminates suitable for use in articles used to absorb, distribute and retain body liquids, such as disposable diapers, sanitary napkins, incontinence garments, and the like, and to a method and apparatus for making the same.

Nonwoven materials, such as spunbonded webs and carded webs, have been used as bodyside liners in disposable absorbent articles. Typically, very open, porous liner structures have been employed to allow liquid to pass through them rapidly, thereby keeping the wearer's skin separate from the wetted absorbent core underneath the liner. Also, other layers of material, such as those constructed with thick, lofty fabric structures, have been interposed between the liner and absorbent pad for the purposes of handling surges of liquids and reducing flow back of liquids.

Previous methods and apparatus for aperturing nonwoven webs, which have been used as bodyside liners in disposable absorbent articles, have created openings in the nonwoven webs which are larger than the spaces between the fibers in the nonwoven webs. The prior methods and apparatus have often included the use of rotating rolls having projections extending therefrom. The projections are often heated and are used to pierce the webs to form apertures within the webs. The heated projections have been used to create fused perimeters around the resultant apertures. The apertured bodyside liners of the prior art purportedly improve fluid intake rates and improve the handling of low-viscosity fecal material. The previous methods and apparatus have generally been designed to aperture relatively thin webs.

However, aperturing lofty or thick nonwoven webs may be desirable for various reasons, such as, for example, to create three-dimensional topography and/or to improve the aesthetics of the nonwoven materials. Previous methods and apparatus are less effective when aperturing lofty or thick nonwovens because the apertures tend to close once the projections are removed from the lofty web. Additionally, tension in the lofty nonwoven web also tends to close the apertures made by traditional methods and apparatus. Finally, previous methods and apparatus tend to compress the entire fibrous nonwoven web.

Therefore there is a need for a method and apparatus to create lofty nonwoven webs containing apertures that are well defined and remain well defined after processing and handling. There is also a need for a method and apparatus to create lofty nonwoven webs having apertures wherein the non-apertured portions remain lofty thereby creating three-dimensional topography in the lofty nonwoven web.

SUMMARY OF THE INVENTION

In response to the needs discussed above, the present invention provides a method and apparatus for bonding and aperturing one or more fibrous webs, the resultant bonded and apertured one or more fibrous webs and absorbent articles incorporating the resultant bonded and apertured one or more fibrous webs.

One method for aperturing a fibrous web includes providing a fibrous web having a plurality of at least partially unbonded fibers. The method includes moving the fibrous web through a bonding nip created by a rotatable bonding roll and a rotatable anvil roll. The rotatable bonding roll has a peripheral bonding surface and a plurality of protuberances extending from the peripheral bonding surface. The plurality of protuberances define a bonding pattern. The method further includes bonding the fibrous web with the plurality of protuberances at a plurality of highly bonded regions. The plurality of highly bonded regions is surrounded by at least one less bonded region. The at least partially unbonded fibers of the fibrous web are plasticized at the plurality of highly bonded regions. The at least partially unbonded fibers of the fibrous web remain at least partially unbonded at the at least one less bonded region. The method further includes moving the fibrous web, with the plurality of highly bonded regions, through an aperturing nip created by a rotatable aperture roll and the rotatable anvil roll. The rotatable aperture roll has a peripheral aperture surface and a plurality of projections extending from the peripheral aperture surface. The plurality of projections define an aperturing pattern. The aperturing pattern substantially aligns with the bonding pattern. The method further includes aperturing the fibrous web at at least 50 percent of the plurality of highly bonded regions with the plurality of projections to create apertures within the at least 50 percent of the highly bonded regions.

In various embodiments, the fibrous web may have a density of less than 0.025 g/cc and a basis weight of at least 40 gsm.

In various embodiments, the bonding roll may be a pressure bonder, thermal bonder or ultrasonic bonder.

In various embodiments, the apertured highly bonded regions may include a single aperture located therein.

In various embodiments, the apertured highly bonded regions each define a center and have an aperture located at the center.

In various embodiments, the apertured highly bonded regions each have an aperture located completely within the highly bonded region.

In various embodiments, the at least one less bonded region may be substantially free of apertures.

One method for bonding and aperturing two or more fibrous webs includes providing first and second fibrous webs having a plurality of at least partially unbonded fibers. The method includes moving the first and the second fibrous webs in facing relation through a bonding nip created by a rotatable bonding roll and a rotatable anvil roll. The rotatable bonding roll has a peripheral bonding surface and a plurality of protuberances extending from the peripheral bonding surface. The plurality of protuberances defines a bonding pattern. The method further includes bonding the first and second fibrous webs together in the bonding nip to create a composite web. The bonding occurs at least at a plurality of highly bonded regions. The plurality of highly bonded regions is surrounded by at least one less bonded region. The method further includes moving the composite web through an aperturing nip created by a rotatable aperture roll and the rotatable anvil roll. The rotatable aperture roll has a peripheral aperture surface and a plurality of projections extending from the peripheral aperture surface that define an aperturing pattern. The aperturing pattern substantially aligns with the bonding pattern thereby aperturing the composite web at at least 50 percent of the highly bonded regions.

In various embodiments, the first fibrous web may have a density of at least 0.05 g/cc and a basis weight of less than 25 gsm and the second fibrous web may have a density of less than 0.025 g/cc and a basis weight of at least 40 gsm.

In various embodiments, the bonding roll is a pressure bonder, thermal bonder or ultrasonic bonder.

In various embodiments, each apertured highly bonded region includes a single aperture located therein.

In various embodiments, each apertured highly bonded region defines a center and has an aperture located at the center.

In various embodiments, the apertured highly bonded regions have apertures located completely within the apertured highly bonded regions.

In various embodiments, the less bonded region is substantially free of apertures.

In various embodiments, the aperturing step may further include removing a portion of the composite web at one or more of the highly bonded regions to create one or more of the apertures.

One diaper includes a bodyside composite, an outercover and an absorbent core positioned between the bodyside composite and the outercover. The bodyside composite includes a bodyside liner and a surge layer. The surge layer is bonded with the liner at a plurality of highly bonded regions. The highly bonded regions are surrounded by at least one less bonded region. At least 50 percent of the highly bonded regions have an aperture located entirely within the highly bonded region.

In various embodiments, the apertures are located concentrically within the highly bonded regions.

One apparatus for bonding and aperturing one or more fibrous webs includes a rotatable anvil roll having a peripheral anvil surface and a rotatable bonding roll. The rotatable bonding roll has a peripheral bonding surface and a plurality of protuberances extending from the peripheral bonding surface. The plurality of protuberances define a bonding pattern and are adapted to pass proximate the peripheral anvil surface thereby forming a bonding nip. The plurality of protuberances are adapted to create a plurality of highly bonded regions in at least one fibrous web moving through the bonding nip. The apparatus further includes a rotatable aperture roll having a peripheral aperture surface and a plurality of projections extending from the peripheral aperture surface. The plurality of projections define an aperturing pattern and are adapted to pass proximate the peripheral anvil surface thereby forming an aperturing nip. The plurality of projections are substantially aligned with the plurality of protuberances to aperture the fibrous web at the plurality of highly bonded regions.

In various embodiments, the rotatable anvil roll is operatively connected with both the rotatable bonding roll and the rotatable aperture roll to mechanically register the plurality of projections with the plurality of highly bonded regions.

In various embodiments, the plurality of projections are cutters adapted to remove a portion of the one or more fibrous webs at the plurality of highly bonded regions.

In various embodiments, the anvil roll is a hole roll machined with a female pattern design.

BRIEF DESCRIPTION OF THE DRAWINGS

The method, apparatus and product of this invention will be better understood by reference to the following description of the invention taken in conjunction with the accompanying drawings.

DETAILED DESCRIPTION

Figure 1:
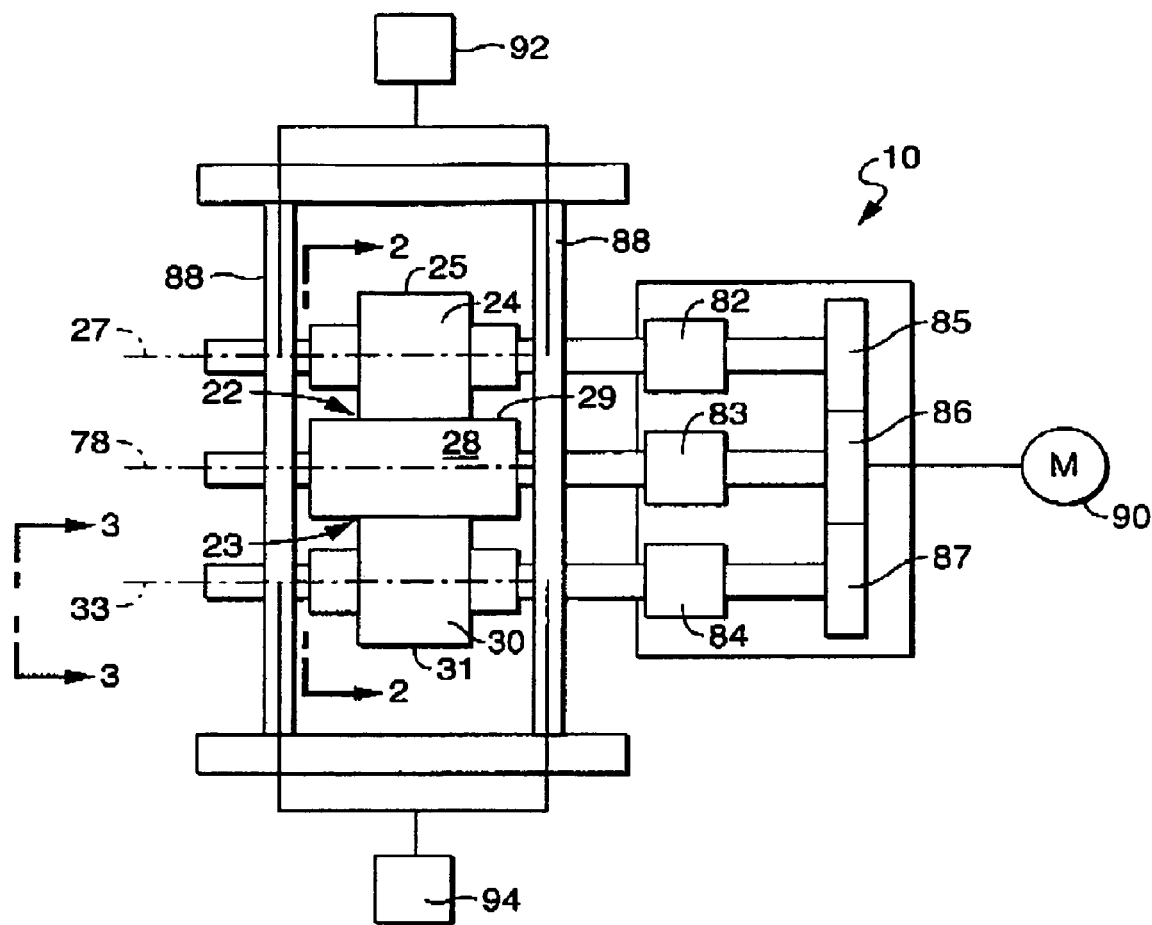
FIG. 1 is a schematic in-line view of the apparatus of the present invention.

The present invention comprehends one or more fibrous fabrics or materials having a plurality of staple fibers and/or continuous filaments. The plurality of staple fibers and/or continuous filaments may comprise one or more thermoplastic materials, preferably thermoplastic polymers. The present invention comprehends a method and apparatus for bonding and aperturing the one or more fibrous fabrics or materials. The present invention additionally comprehends the use of the one or more bonded and apertured fibrous fabrics or materials as at least one component in a disposable absorbent garment.

The present invention comprehends a single fibrous fabric or material, which can be a nonwoven web, being bonded in a spaced apart bonding pattern, such as by thermal bonding between a pair of heated embossing or bonding rolls, at least one of the pair having raised bonding patterns on the outer surface thereof. This spaced apart bonding pattern provides high structural integrity within the fibrous web without compromising the flexibility and or the loftiness of the resulting fibrous web. Apertures are formed in one or more of the spaced apart bonding areas to make the apertures more visible and to maintain the apertures after formation. The fibrous web formed in accordance with the present invention is believed to improve liquid intake and distribution and air circulation characteristics, resulting in greater surface dryness and comfort when placed against or proximate human skin.

The present invention also comprehends two or more fibrous fabrics or materials, which can be nonwoven webs, being joined into a fibrous composite by a spaced apart bonding pattern, such as by thermal bonding between a pair of heated embossing or bonding rolls, at least one of the pair having raised bonding patterns on the outer surface thereof. This spaced apart bonding pattern provides high structural integrity between the first and second fibrous webs without compromising the flexibility, soft surface texture or the loftiness of the resulting fibrous composite web. Apertures are formed in one or more of the spaced apart bonding areas to make the apertures more visible and to maintain the apertures after formation. The fibrous composite formed in accordance with the present invention is believed to improve liquid intake and distribution and air circulation characteristics, resulting in greater surface dryness and comfort when placed against or proximate human skin.

The fibrous web or composite web of this invention provides three-dimensional surface topology, that is, a lofty, pillowed structure that is believed to improve softness, aesthetics and provide a cushiony feel to the user. Other attributes and advantages of the present invention will be apparent from the ensuing disclosure and appended claims.

As used herein, the terms "nonwoven web" and "nonwoven layer" mean a fibrous web or layer having a structure of individual fibers or filaments that are interlaid in a random pattern. Nonwoven webs have been formed in the past by a variety of processes, such as, for example, meltblowing, spunbonding, airlaying, wetlaying, drylaying, dry staple and carded web processes. While nonwoven webs can be used in practicing the present invention, the invention is not to be considered limited to nonwoven materials and other suitable fibrous structures may be employed.

The fibrous web or composite web of this invention will be described herein as used in disposable absorbent articles. However, it should be understood that potential applications of this invention need not be limited to such disposable absorbent articles. As used herein, the term "disposable absorbent article" means an article that is used to absorb and retain body exudates and is intended to be discarded after a limited period of use. Such articles can be placed against or in close proximity to the body of the wearer to absorb and retain various exudates discharged from the body.

Figure 2B:
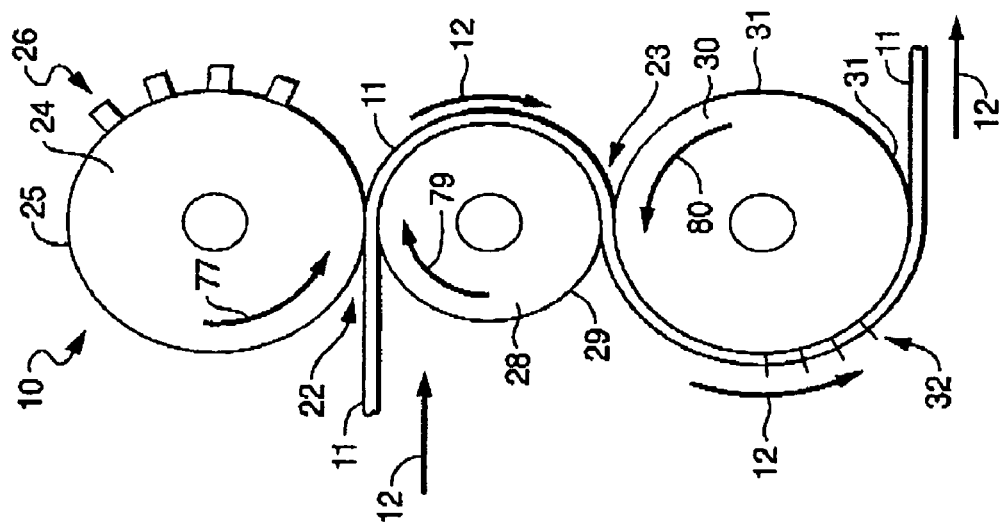
FIG. 2B is a schematic side view of the apparatus of FIG. 1 illustrating an alternative web path taken along the line 2-2.
Figure 2A:
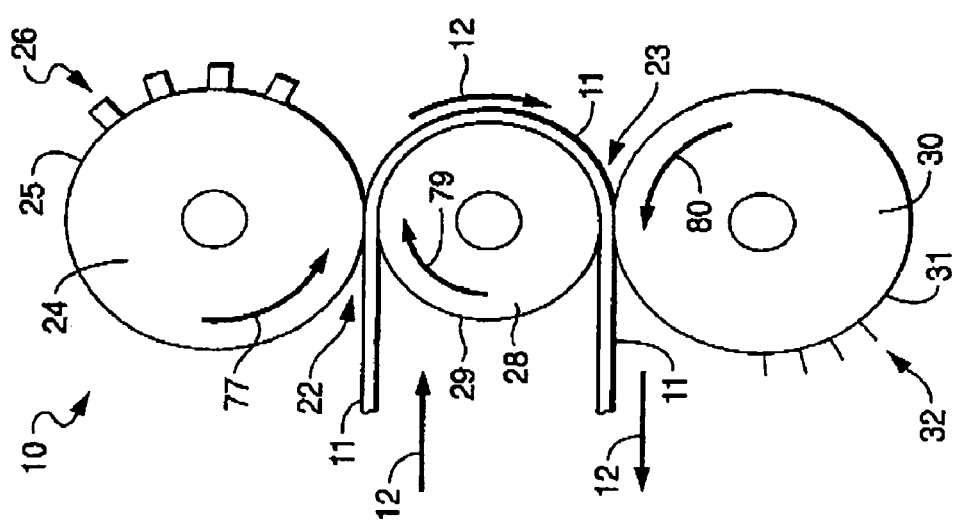
FIG. 2A is a schematic side view of the apparatus of FIG. 1 illustrating an alternative web path taken along the line 2-2.

FIGS. 1, 2A, and 2B representatively illustrate apparatus for bonding and aperturing one or more fibrous webs. FIG. 1 is an in-line schematic view of exemplary apparatus of the present invention. FIG. 2A is an end view schematic taken along line 2-2 of FIG. 1 and representatively illustrates a first alternative web path. FIG. 2B is an end view taken along line 2-2 of FIG. 1 and representatively illustrates a second alternative web path. The apparatus, which is generally indicated at 10, includes a rotatable anvil roll 28, a rotatable bonding roll 24 and a rotatable aperturing roll 30. The rotatable bonding roll 24 is located adjacent a web path 11. The web path 11 is configured to allow the one or more fibrous webs to move along the web path 11. The bonding roll 24 is configured to rotate about a bonding axis 27 in the direction indicated by the arrow 77 associated therewith. The bonding roll 24 has an outer peripheral bonding surface 25. The outer peripheral bonding surface 25 has a plurality of protuberances 26 extending from the peripheral bonding surface 25, the plurality of protuberances 26 defining a bonding pattern.

The rotatable anvil roll 28 has an outer peripheral anvil surface 29 upon which one or more fibrous webs may travel. The rotatable anvil roll 28 is located adjacent the web path 11 and forms a bonding nip 22 with the bonding roll 24. The anvil roll 28 is configured to rotate about an anvil axis 78 in the direction indicated by the arrow 79 associated therewith. The rotatable anvil roll 28 may be a smooth surfaced cylinder of steel or alternatively may be a hole roll which has been machined or engraved with a female pattern design.

The plurality of protuberances 26 are disposed in a predetermined bonding pattern. Each protuberance 26 is configured and disposed to precipitate a highly bonded region or bond site in the one or more fibrous webs being produced. The plurality of protuberances 26 precipitate the highly bonded regions in the one or more fibrous webs as the one or more fibrous webs pass through the bonding nip 22.

The protuberances 26 may be an integral portion of the bonding roll 24. As such, the bonding roll 24 and protuberances 26 may be machined by starting with a circular cylinder and removing surrounding metal. Alternatively, the protuberances 26 may be separate components operatively attached to the bonding roll 24. The protuberances 26 may be operatively attached by bolts, welds, screws, press fittings, a matching key and keyway, and the like, and combinations thereof.

The protuberances 26 may have substantially vertical side surfaces and project radially outward a distance. Alternatively, the protuberances 26 may have tapered side surfaces such that the cross sectional area of the protuberances 26 is greater at locations near the peripheral bonding surface 25 than at locations more remote from the peripheral bonding surface 25. The distance is the radial height of the protuberance 26 and may be any suitable length depending on the characteristics of the one or more fibrous webs being bonded. In various embodiments, the distance may be from about 0.125 mm to about 15 mm. In particular embodiments, the distance may be 1.5 mm to 2.5 mm.

The protuberances 26 may have a chamfered or rounded edge at the end remote from the bonding roll 24. Alternatively, the protuberances 26 may have a generally right angle edge at the end remote from the bonding roll 24. The protuberances 26 may have a circular planform with a diameter measured at the end remote from the bonding roll 24 of any suitable dimension. In particular embodiments, the diameter may be about 3 mm to about 10 mm.

In various embodiments, the apparatus 10 may include protuberances 26 having planforms that are rectangular, oval, circular, triangular, irregular, linear, arcuate, and the like and combinations thereof. The protuberances 26 may have cross sectional areas at the end remote from the bonding roll 24 having an area of any suitable dimension. In various embodiments, the cross sectional area may be from 7 mm$^2$ to 100 mm$^2$. The protuberances 26 may be arranged in a predetermined bonding pattern. The bonding pattern may be intermittent or may be continuous. As used herein, the term "intermittent" describes a pattern that does not extend around the entire circumference of the peripheral surface of a given roll (e.g., FIGS. 2A and 2B). Conversely, the term "continuous" describes a pattern that does extend around the entire circumference of the peripheral surface of a given roll (e.g., FIG. 3A).

The rotatable aperture roll 30 is located adjacent the web path 11 and forms an aperturing nip 23 with an anvil roll, preferably the anvil roll 28. The rotatable aperture roll 30 has an outer peripheral aperture surface 31 upon which one or more fibrous webs may travel. The peripheral aperture surface 31 may have a plurality of projections 32 extending therefrom. The plurality of projections 32 define an aperturing pattern. The aperturing pattern substantially aligns with the bonding pattern. As used herein, the term "substantially aligns" means having elements that are equally spaced on the same repeat length in the machine direction and are the same distance from a common reference in the cross machine direction. For example, two patterns having five elements equally spaced in the machine direction within a 10 mm repeat length and having all elements 300 mm from a common reference in the cross machine direction would be substantially aligned. The aperture roll 30 is configured to rotate about an aperture axis 33 in the direction indicated by the arrow 80 associated therewith.

In various embodiments, the plurality of projections 32 are disposed in a predetermined aperturing pattern. The aperturing pattern may be continuous or intermittent. Each projection 32 is configured and disposed to precipitate an aperture in the highly bonded region or bond site in the one or more fibrous webs being produced. The plurality of projections 32 precipitates the apertures in the one or more fibrous webs as the one or more fibrous webs pass through the aperturing nip 23.

The projections 32 may be an integral portion of the aperturing roll 30. As such, the aperturing roll 30 and projections 32 may be machined by starting with a circular cylinder and removing surrounding metal. Alternatively, the projections 32 may be separate components operatively attached to the aperturing roll 30. The projections 32 may be operatively attached by bolts, welds, screws, press fittings, a matching key and keyway, and the like, and combinations thereof.

The projections 32 may have substantially vertical side surfaces and project radially outward a distance. The distance is the radial height of the projections 32. In various embodiments, the distance may be 0.125 mm to 10 mm. The projections 32 may be aperturing pins held about the peripheral aperturing surface 31 by one or more pin plates adapted to hold a plurality of aperturing pins and bolt to the aperturing roll 30. By using the pin plates various pin patterns may be accomplished using a single aperturing roll 30. The aperturing pins may have a variety of shapes and sizes as are known in the art. Exemplary aperturing methods and apparatus are described in U.S. Pat. No. 4,886,632 issued Dec. 12, 1989 to Van Iten et al., the entirety of which is incorporated herein by reference where not contradictory. In various embodiments, the projections 32 may have diameters of 0.3 mm to 10 mm. In particular embodiments, the projections 32 may have diameters of 1 mm to 2.5 mm. In various embodiments, the projections 32 may be essentially the same as the protuberances 26 described herein and adapted to completely penetrate the one or more fibrous webs being produced.

Figure 3A:
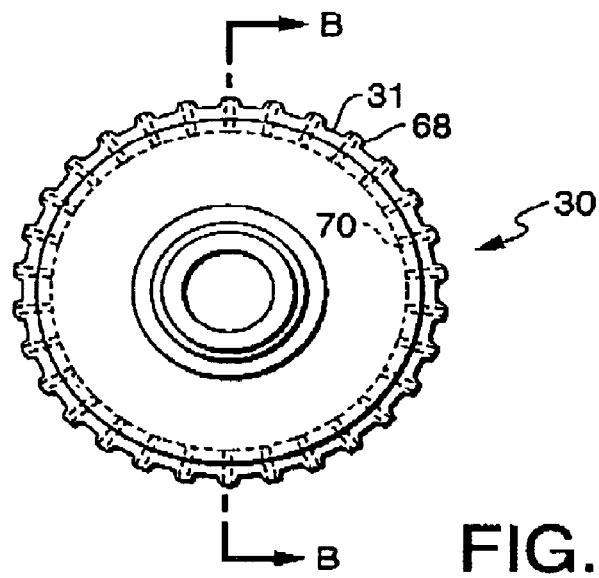
FIG. 3A is a side view of the apparatus of FIG. 1 taken along the line 3-3.
Figure 3B:
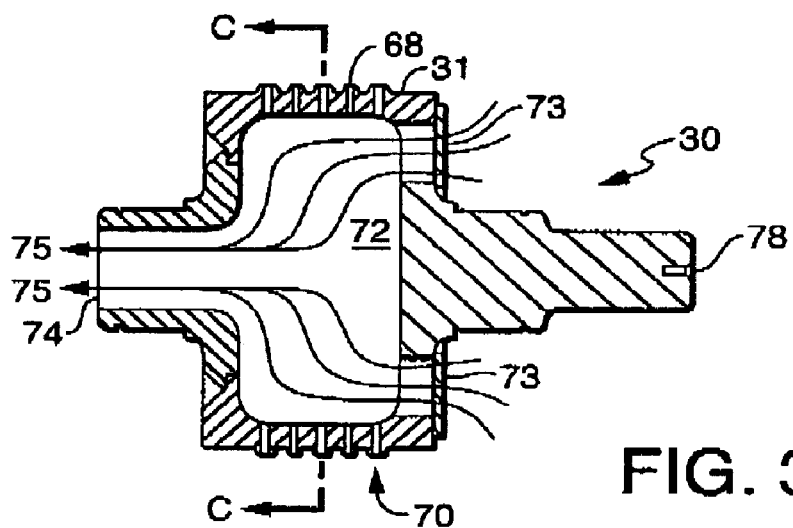
FIG. 3B is a cross sectional view of the apparatus of FIG. 3A taken along the line B-B.
Figure 3C:
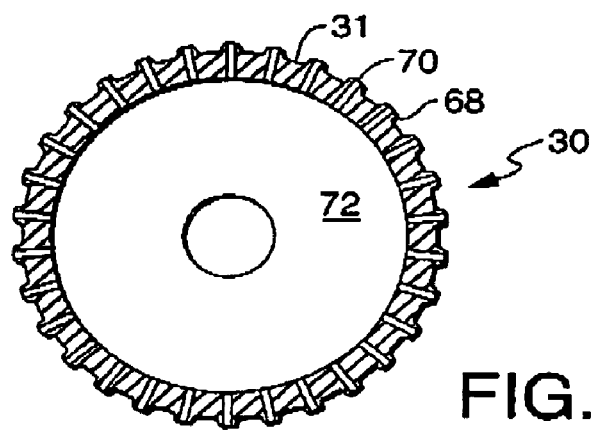
FIG. 3C is a cross sectional view of the apparatus of FIG. 3B taken along the line C-C.

The projections 32 may alternatively be cutters adapted to create apertures by removing material from the one or more fibrous webs being produced, as compared to only piercing the one or more fibrous webs as occurs with pins. FIG. 3A is an end view of an alternative aperture roll 30 taken along the line 3-3 of FIG. 1. The aperture roll 30, in this embodiment, may include cone shaped cutters 68 extending laterally from the peripheral aperture surface 31. FIG. 3B is a cross sectional view of the aperture roll 30 of FIG. 3A taken along the line B-B. FIG. 3C is a cross sectional view of the aperture roll 30 of FIG. 3B taken along the line C-C. As illustrated in FIGS. 3B and 3C, the aperture roll 30 includes a central cavity 72, one or more inlets 73 and one or more outlets 74.

The cutters 68 may be generally circular and have passages 70 within the centers of the cutters 68. Alternatively, the cutters 68 may have a shape that is oblong, oval, rectangular, irregular, and the like, and combinations thereof. The passages 70 extend to and connect with the central cavity 72. The cutters 68 are configured to cut a discrete piece of material from the one or more fibrous webs at the one or more high bonding regions. The passages 70 are configured to allow passage of the discrete pieces of material into the central cavity 72. The one or more inlets 73 are configured to provide airflow to the central cavity 72. The air moving through the central cavity 72 may be adapted, such as by vacuum or pressure, to entrain the discrete pieces of material cut from the one or more fibrous webs. The one or more outlets 74 are configured to allow the air and the discrete pieces of material to be removed from the central cavity 72 in a direction 75.

The web path 11 includes, at least in part, the bonding nip 22 and the aperturing nip 23. In various embodiments, the web path 11 may also include portions of the peripheral bonding surface 25 and/or portions of the peripheral anvil surface 29 and/or the peripheral aperturing surface 31, as illustrated in FIGS. 2A and 2B.

The bonding roll 24 and/or the anvil roll 28 and/or the aperture roll 30 may be connected to a shaft by suitable means such as by welds, bolts, screws, press fittings, a matching key and keyway, and the like, and combinations thereof. The bonding roll 24 and/or the anvil roll 28 and/or the aperture roll 30 may then be rotatably mounted and connected to a frame support 88 by suitable means such as, for example, conventional bearings.

Typically the bonding roll 24 and/or the anvil roll 28 and/or the aperture roll 30 are driven by any means known to those skilled in the art such as, for example, an electric motor 90. The bonding roll 24 and/or the anvil roll 28 and/or the aperture roll 30 can be made from any material that is capable of withstanding the forces exerted in the bonding nip 22 and the aperturing nip 23. Desirably, the bonding roll 24 and/or the anvil roll 28 and/or the aperture roll 30 are made from steel. In various embodiments, the bonding roll 24 and/or the anvil roll 28 and/or the aperture roll 30 may be heated.

The bonding roll 24, the anvil roll 28 and the aperture roll 30 may be driven separately, such as, for example, by using servo drives with registration and feedback control, i.e., electronic coupling. However, the bonding roll 24, the anvil roll 28 and the aperture roll 30 are desirably operatively connected such that the rolls are driven together. As used herein, the term "operatively connected" means that each of the bonding roll 24, the anvil roll 28 and the aperture roll 30 are physically linked such that the aperturing pattern is mechanically registered to the bonding pattern.

Referring again to FIG. 1, the apparatus 10 may further include a bonding coupling 82 and/or an anvil coupling 83 and/or an aperture coupling 84. The apparatus 10 may also include a bonding gear 85 and/or an anvil gear 86 and/or an anvil gear 87. The motor 90 may be configured to drive any or all of the bonding gears 85, 86 and 87 which in turn may be configured to drive any or all of the couplings 82, 83 and 84 which in turn may be configured to rotate any or all of the rolls 24, 28 and 30.

The bonding coupling 82 and/or the anvil coupling 83 and/or the aperture coupling 84 may be in-line couplings. One suitable in-line coupling is the Schmidt In-Line L400 Series Couplings available from Zero-Max, Inc., having offices in Plymouth, Minn., USA. Alternatively, the bonding coupling 82 and/or the anvil coupling 83 and/or the aperture coupling 84 may be offset couplings. One suitable offset coupling is the Schmidt Offset L200 Series Couplings available from Zero-Max, Inc., having offices in Plymouth, Minn., USA. In a particular embodiment, the bonding coupling 82 and the aperture coupling 84 may be offset couplings and the anvil coupling 83 may be an in-line coupling.

The bonding gear 85, the anvil gear 86 and the aperturing gear 87 may be interconnected by tooth to tooth meshing.

Alternatively, the gears 85, 86 and 87 may be interconnected by a double sided toothed belt. In either alternative, the ratio of the gears 85, 86 and 87 are preferably exact integers. For example, the gear ratio of the bonding gear 85 to the anvil gear 86 to the aperturing gear 87 may be, for example, 1 to 1 to 1, 1 to 2 to 1, 1 to 2 to 3, 3 to 1 to 3, etc. thereby ensuring mechanical registration.

Use of the offset couplings allow the bonding nip 22 and the aperturing nip 23 to be opened without disengaging the gears 85, 86 and 87. This advantageously maintains mechanical registration between the bonding roll 24 and the aperture roll 30 and ensures the bonding pattern and aperturing pattern remain substantially aligned. In various embodiments, one or more of the gears 85, 86 and/or 87 may include anti-backlash designs as are known in the art.

The apparatus 10 may also include a bonding pressuring means 92 connected, directly or indirectly, to the bonding roll 24 for exerting force on the one or more fibrous webs and for exerting force on the anvil roll 28 in the bonding nip 22. The bonding pressuring means 92 should be capable of exerting a force sufficient to maintain contact between the bonding roll 24 and the anvil roll 28. Preferably, the bonding pressure means 92 is capable of exerting from about 80,000 pounds per square inch (psi) to about 150,000 psi between the bonding roll 24 and the anvil roll 28. Any mechanism capable of exerting the desired amount of force on the one or more fibrous webs and the anvil roll 28 is suitable. For example, an air cylinder and/or a hydraulic cylinder may be connected to the bonding roll 24. The air cylinder and/or the hydraulic cylinder may be configured to exert an actuating force on the anvil roll 28. The bonding pressuring means 92 provides the ability to control the amount of pressure in the bonding nip 22.

The apparatus 10 may also include an aperturing pressuring means 94 connected, directly or indirectly, to the aperturing roll 30 for exerting force on the one or more fibrous webs and for exerting force on the anvil roll 28 in the aperturing nip 23. The aperturing pressuring means 94 should be capable of exerting a force sufficient to maintain contact between the aperture roll 30 and the anvil roll 28. In some embodiments, the aperturing pressure means 94 may be capable of exerting from about 80,000 pounds per square inch (psi) to about 150,000 psi between the aperturing roll 30 and the anvil roll 28. Any mechanism capable of exerting the desired amount of force on the one or more fibrous webs and the anvil roll 28 is suitable. For example, an air cylinder and/or a hydraulic cylinder may be connected to the aperturing roll 30. The air cylinder and/or the hydraulic cylinder may be configured to exert an actuating force on the anvil roll 28. The aperturing pressuring means 94 provides the ability to control the amount of pressure in the aperturing nip 23.

The apparatus 10 may also include one or more temperature controllers for independently heating one or more of the bonding roll 24, anvil roll 28 and the aperture roll 30.

In various embodiments, the aperture roll 30 may alternatively be a pressure bonding roll having a plurality of protuberances set to bond "through" the web thereby creating apertures. In various embodiments, the apparatus 10 may further include one or more additional bonding rolls to create one or more additional bonding patterns. The one or more additional bonding rolls may form one or more additional bonding nips with one or more additional anvil rolls, preferably with the anvil roll 28. The one or more additional bonding rolls may be registered with an aperture roll as discussed herein. Preferably, the one or more additional bonding rolls are mechanically registered with the aperture roll 30.

Figure 4:
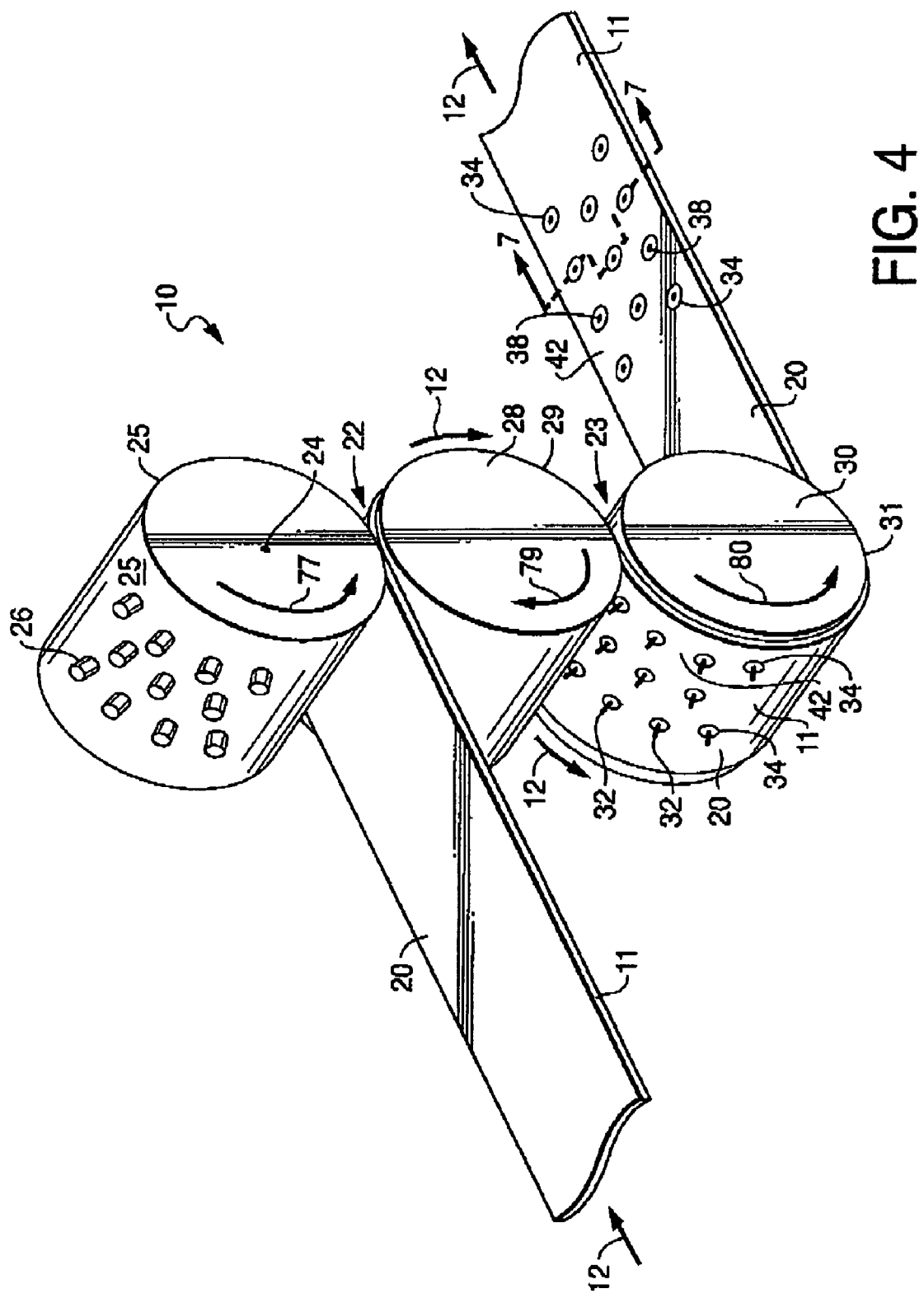
FIG. 4 representatively illustrates a first perspective view of exemplary apparatus, method and product of the present invention.
Figure 5:
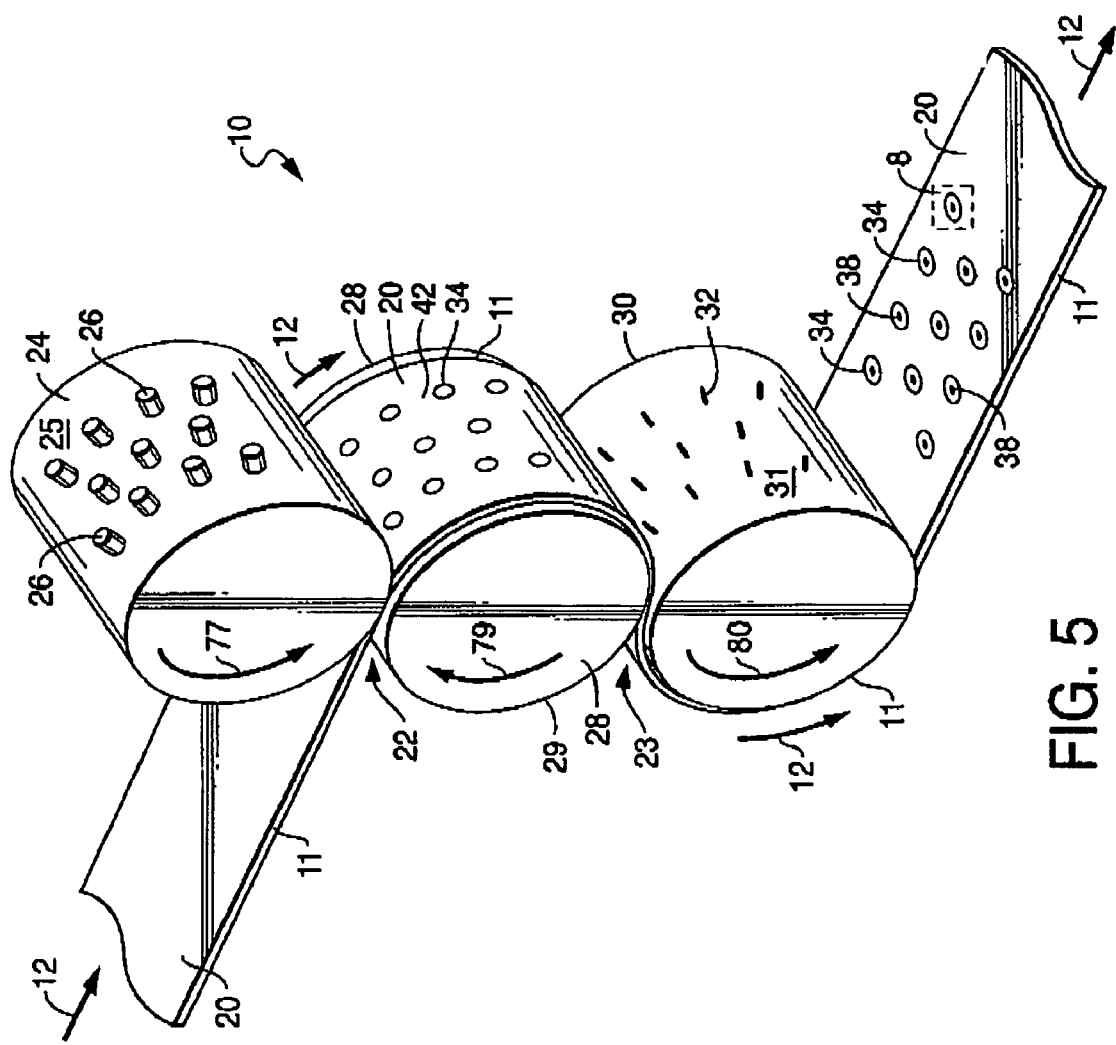
FIG. 5 representatively illustrates a second perspective view of the apparatus, method and product illustrated in FIG. 4.

Referring now FIGS. 4 and 5, a method and the apparatus 10 for bonding and aperturing a fibrous web is representatively illustrated. FIG. 4 representatively illustrates a first perspective view of the method and the apparatus 10 with the supporting apparatus and drive apparatus removed for clarity and with the entrance side of the bonding nip 22 and exit side of the aperturing nip 23 facing the viewer. FIG. 5 representatively illustrates a second perspective view of the method and apparatus 10 with the supporting apparatus and drive apparatus removed for clarity and with the exit side of the bonding nip 22 and the entrance side of the aperturing nip 23 facing the viewer. In both FIGS. 4 and 5, the web path 11 is illustrated as including a portion of the peripheral anvil surface 29 and a portion of the peripheral aperture surface 31. The apparatus 10 and method may be used to bond and aperture a continuously moving fibrous web 20. The fibrous web 20 may include fibers that are at least partially unbonded. As used herein, the term "at least partially unbonded" means that the fibers that comprise the fibrous web 20 have portions that are not connected or fused to adjacent fibers, are individually discernable under magnification and have at least some open space between individual fibers.

The fibrous web 20 is continuously moved along the web path 11 in the direction indicated by the arrow 12 associated therewith. The rotatable bonding roll 24 rotates in the direction indicated by the arrow 77 associated therewith. The fibrous web 20 contacts the peripheral bonding surface 25 and the peripheral anvil surface 29 in the bonding nip 22. The rotatable anvil roll 28 rotates in the direction indicated by the arrow 79 associated therewith. The fibrous web 20 moves through the bonding nip 22 in the direction 12 moving from the entrance side to the exit side of the bonding nip 22. The peripheral bonding surface 25, and in particular the plurality of protuberances 26, of the bonding roll 24, press the fibrous web 20 against the peripheral anvil surface 29 of the anvil roll 28 in the bonding nip 22 thereby bonding the fibrous web 20 at a plurality of highly bonded regions 34. As used herein the term "bonding" means to permanently connect adjacent fibers by means of melting, fusing, and the like, and combinations thereof.

The plurality of highly bonded regions 34 correspond with the bonding pattern defined by the plurality of protuberances 26. The at least partially unbonded fibers of the fibrous web 20 are at least partially plasticized in the plurality of highly bonded regions 34. Desirably, the at least partially unbonded fibers of the fibrous web 20 are completely plasticized in the plurality of highly bonded regions 34. As used herein, the term "plasticized" refers to fibers that have been bonded together such that the fibers are no longer individually discernable and have essentially become a film. To plasticize the fibers may include, but does not require, melting the fibers such that the material flows.

As the fibrous web 20 exits the bonding nip 22, the plurality of highly bonded regions 34 are surrounded by at least one less bonded region 42. The at least partially unbonded fibers of the fibrous web 20 remain at least partially unbonded in the less bonded region 42.

The fibrous web 20 moves along the web path 11, which includes a portion of the peripheral anvil surface 29, in the direction indicated by arrow 12, to the anvil nip 23. The aperture roll 30 rotates in the direction indicated by the arrow 80 associated therewith. As the aperture roll 30 rotates, the projections 32 come into contact with the fibrous web 20 and penetrate or cut the fibrous web 20 as the fibrous web moves through an aperturing nip, preferably the aperturing nip 23, from the entrance side to the exit side. The plurality of projections 32, in conjunction with the anvil surface 29 of the anvil roll 28, create one or more apertures 38 corresponding to the aperturing pattern in the fibrous web 20. Because the aperturing pattern substantially aligns with the bonding pattern, the one or more apertures 38 substantially align with the one or more highly bonded regions 34. The aperturing pattern is preferably aligned with the bonding pattern by operatively connecting and thereby mechanically registering the bonding roll 24, the anvil roll 28 and the aperture roll 30 with one another.

Figure 6:
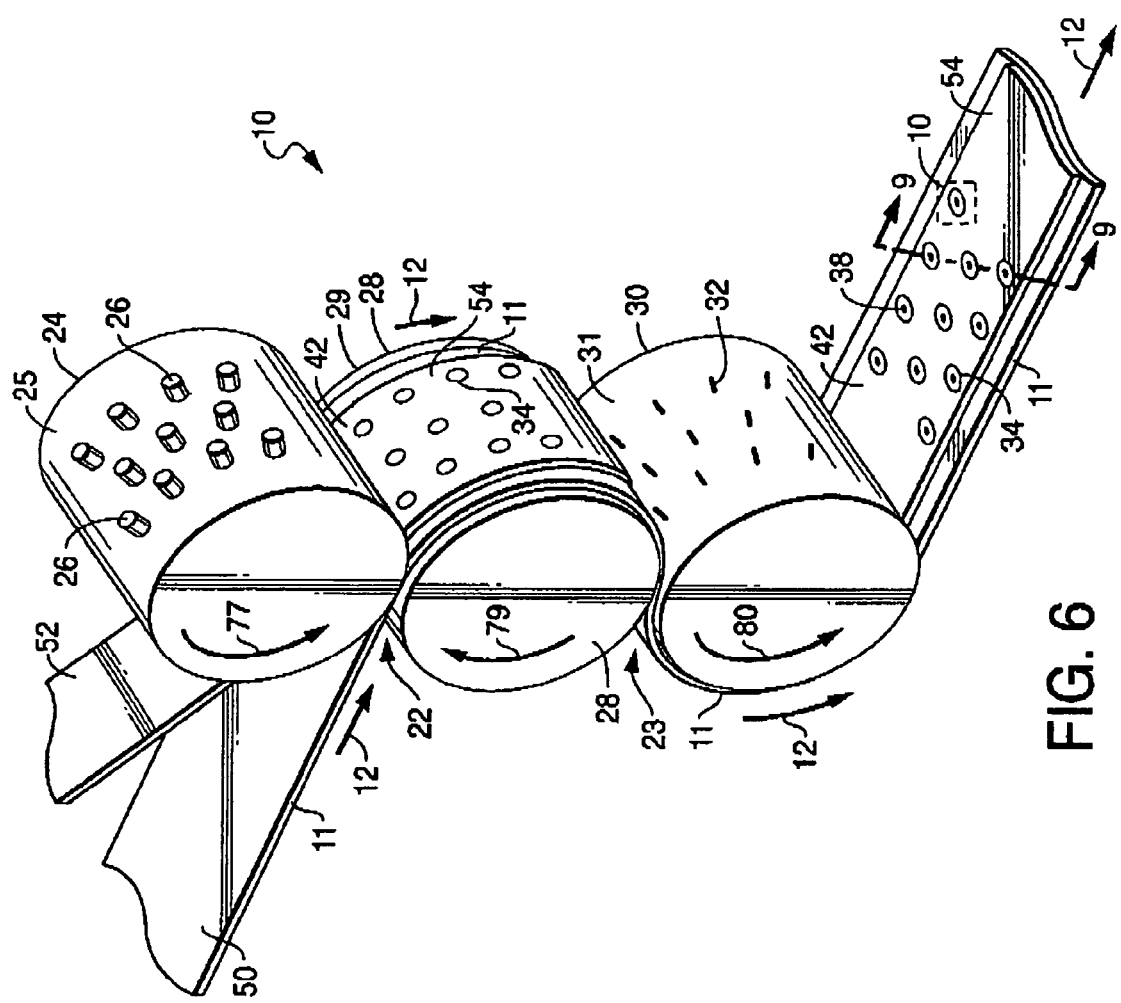
FIG. 6 representatively illustrates a perspective view of exemplary apparatus, method and product of the present invention.

Referring now to FIG. 6, a method and apparatus for bonding and aperturing first and second fibrous webs is representatively illustrated. The apparatus, which is generally indicated at 10, is generally the same as that described above. The method and apparatus of the present invention may be used to bond and aperture first and second continuously moving fibrous webs 50 and 52. The fibrous webs 50 and 52 may include fibers that are at least partially unbonded. Either or both fibrous webs 50 and 52 may be intermittent webs. In a particular embodiment, the second continuously moving fibrous web 52 is cut into discrete pieces and placed at spaced apart locations on the first continuously moving fibrous web 50 prior to entering the bonding nip 22. The second web 52 may be cut and placed by any suitable method and apparatus known in the art, such as, for example, by using a slip cut module.

The fibrous webs 50 and 52 are continuously moving in facing relation along a web path 11 in the direction indicated by the arrow 12 associated therewith. The fibrous webs 50 and 52 move through the bonding nip 22 from the entrance side to the exit side. While in the bonding nip 22, the peripheral bonding surface 25 of the bonding roll 24 presses the fibrous webs 50 and 52 against the peripheral anvil surface 29 of the anvil roll 28 thereby bonding the fibrous webs 50 and 52 together at a plurality of highly bonded regions 34 to create a composite web 54. The composite web 54 includes fibers that are at least partially unbonded. The plurality of highly bonded regions 34 correspond to the plurality of protuberances 26 and are thereby arranged in the bonding pattern. The plurality of highly bonded regions 34 are surrounded by at least one less bonded region 42. The at least partially unbonded fibers of the composite web 54 remain at least partially unbonded in the less bonded region 42 and the at least partially unbonded fibers are at least partially plasticized in the plurality of highly bonded regions 34. Desirably, the at least partially unbonded fibers of the composite web 54 are completely plasticized in the plurality of highly bonded regions 34.

The composite web 54 moves along the web path 11 in the direction 12. The web path 11 includes a portion of the peripheral anvil surface 29. The composite web 54 is moved to an aperture nip, preferably the aperture nip 23. The aperture roll 30 rotates in the direction indicated by the arrow 80 associated therewith. As the aperture roll 30 rotates, the projections 32 come into contact with the composite web 54 and penetrate or cut the composite web 54 as it moves through the aperturing nip 23 from the entrance side to the exit side. The plurality of projections 32, in conjunction with the anvil surface 29 of the anvil roll 28, create apertures 38 corresponding to the aperturing pattern in the composite web 54. Because the aperturing pattern substantially aligns with the bonding pattern, the apertures 38 substantially align with the highly bonded regions 34. The aperturing pattern is preferably aligned with the bonding pattern by operatively connecting and thereby mechanically registering the bonding roll 24, the anvil roll 28 and the aperture roll 30 with one another.

Either the fibrous web 20 or the composite web 54, with apertures 38 substantially aligned with highly bonded regions 34, may move along the web path 11 for subsequent processing, such as, for example, winding or conversion as a component useful in a diaper process. The web path 11 may include portions of the peripheral aperture surface 31 any number of additional rollers, guides, nips, and the like, and combinations thereof.

Adequate bonding, both in a single web and between two or more webs, can be achieved by a variety of mechanisms. For example the bonding in a single web can result from the partial or complete melting of a portion of the fibrous web 20. Bonding between two or more fibrous webs can result from the partial or complete melting of one or both of the first and second fibrous webs 50 and 52. The bonding can also result from the partial or complete melting of only one of the first and second fibrous webs 50 and 52 with the melted material flowing onto the adjacent fibrous web which in turn results in the mechanical interlocking of the fibrous webs to each other. The single fibrous web 20 and/or the first and second fibrous webs 50 and 52 may be melted and bonded by any means known to those skilled in the art, such as, for example, thermally or ultrasonically. Alternatively, the first and second fibrous webs 50 and 52 may be adhesively bonded together by applying an adhesive to at least one of the first and second fibrous webs 50 and 52 before the webs are pressed together using the apparatus and method of the present invention.

In various embodiments, the method further includes pressure biasing the bonding roll 24 and the anvil roll 28 towards each other in the bonding nip 22 with a predetermined protuberance loading and rotating the bonding roll 24 and the anvil roll 28 at the same surface velocity. Alternatively, the bonding roll 24 and the anvil roll 28 may be rotated to provide a surface velocity differential therebetween. In some embodiments, the anvil roll 28 is smooth surfaced and is operated at a surface velocity that is greater than the surface velocity of the bonding roll 24. In other embodiments, the anvil roll 28 is operated at a surface velocity that is equal to, greater than or less than the surface velocity of the bonding roll 24. Bonding may be improved by operating the bonding roll 24 at a different rotational speed as compared to the anvil roll 28 because the shearing forces tangential to the peripheral bonding surface 25 may enable dynamic, mechanically induced, thermal bonding.

Figure 7:
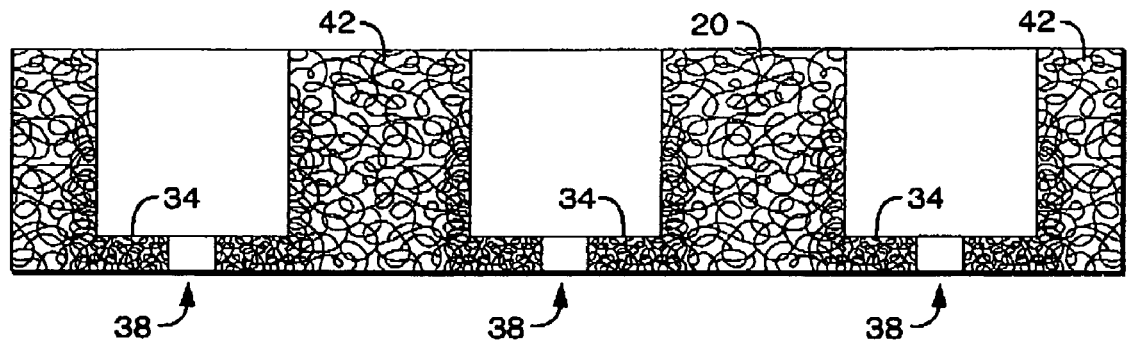
FIG. 7 representatively illustrates a cross sectional view of the product web illustrated in FIG. 4 taken along the line 7-7.

FIG. 7 representatively illustrates a cross sectional view of the fibrous web 20 of FIG. 4 taken along the line 7-7. The fibrous web 20 includes a plurality of highly bonded regions 34 and a less bonded region 42. Each highly bonded region 34 is illustrated with a single aperture 38 located therein.

Figure 8:
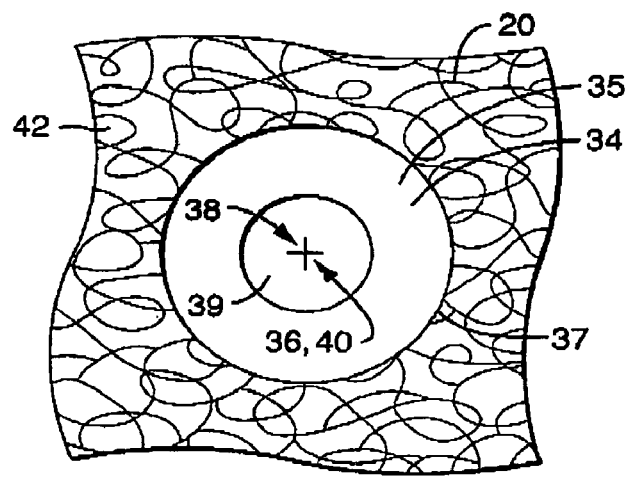
FIG. 8 representatively illustrates a top plan view of a portion of the product web illustrated in FIG. 5 and defined by box 8.

FIG. 8 representatively illustrates a top view of the fibrous web 20 of FIG. 5 and the area defined by box 8. FIG. 8 representatively illustrates a portion of the fibrous web 20 including a single highly bonded region 34 surrounded by a less bonded region 42. The highly bonded region 34 defines a highly bonded area 35, a highly bonded perimeter 37 and a highly bonded center point 36. The highly bonded region 34 includes an aperture 38. The aperture 38 defines an aperture area 39 and an aperture center point 40.

Figure 9:
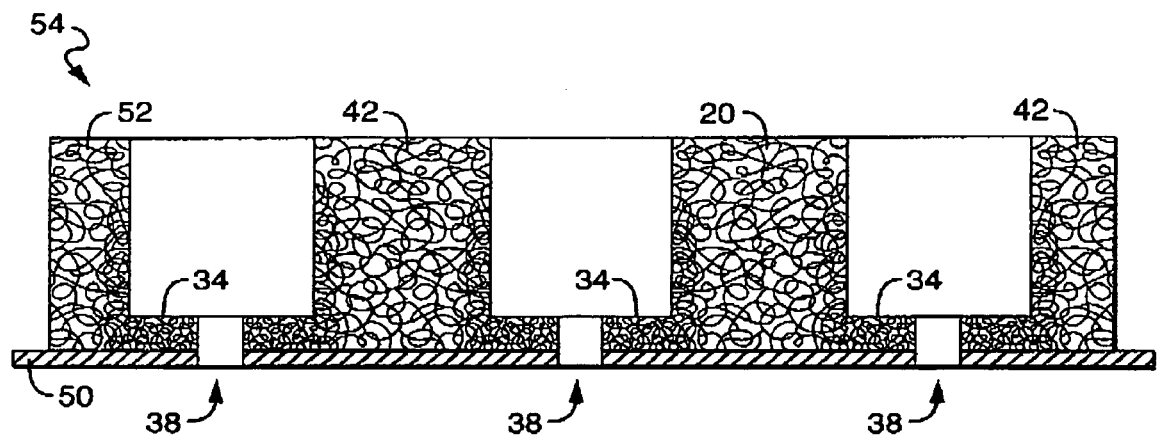
FIG. 9 representatively illustrates a cross sectional view of the composite product web illustrated in FIG. 6 taken along the line 9-9.

FIG. 9 representatively illustrates a cross sectional view of the composite web 54 of FIG. 6 taken along line 9-9. The composite web 54 includes a plurality of highly bonded regions 34 and a less bonded region 42. The composite web 54 includes first fibrous web 50 bonded with the second fibrous web 52 at highly bonded regions 34. Each highly bonded region 34 is illustrated with a single aperture 38 located therein. Each aperture 38 extends through the composite web 54 which includes extending through both the first and the second fibrous webs 50 and 52.

Figure 10:
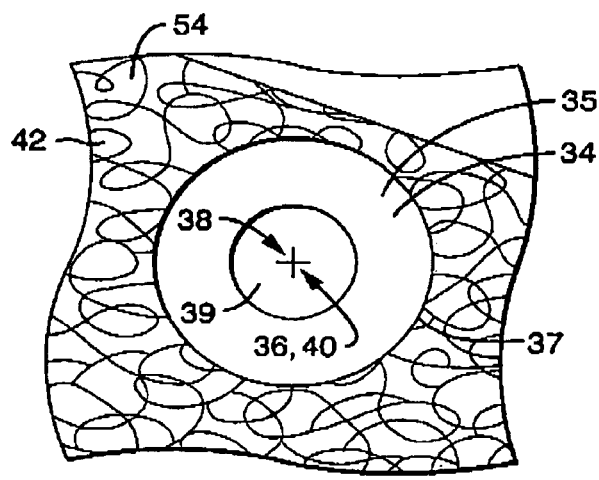
FIG. 10 representatively illustrates a top plan view of a portion of the composite product web illustrated in FIG. 6 and defined by box 10.

FIG. 10 representatively illustrates a top view of the composite web 54 of FIG. 6 and the area defined by box 10. FIG. 10 representatively illustrates a portion of the composite web 54 including a single highly bonded region 34 surrounded by a less bonded region 42. The highly bonded region 34 defines a highly bonded area 35, a highly bonded perimeter 37 and a highly bonded center point 36. The highly bonded region 34 includes an aperture 38. The aperture 38 defines an aperture area 39 and an aperture center point 40.

In various embodiments, the method may further include penetrating or cutting the fibrous web 20 or the composite web 54 such that each highly bonded region 34 includes a single aperture 38 located therein as illustrated in FIGS. 4, 5 and 6. In various embodiments, the method may further include penetrating or cutting the fibrous web 20 or the composite web 54 such that the one or more less bonded region 42 is free of apertures 38 or is substantially free of apertures 38. As used herein, the term "substantially free of apertures" describes a region having less than one aperture per four square inches (25.8 square centimeters) of surface area.

In various embodiments, the method may include penetrating or cutting the fibrous web 20 or the composite web 54 such that each highly bonded region 34 has an aperture 38 located at the center of the highly bonded region 34 as illustrated in FIGS. 4, 5, and 6. For an aperture 38 to be "located at the center" of the highly bonded region 34, the highly bonded region 34 defines a center point 36, each aperture 38 defines an aperture area 39 and the highly bonded region center point 36 is located within the aperture area 39 as illustrated in FIGS. 8 and 10. In various embodiments, at least 90 percent, at least 80 percent, at least 70 percent, at least 60 percent or at least 50 percent of the highly bonded regions 34 have an aperture 38 located at the center of the highly bonded region 34.

In various embodiments, the method may include penetrating or cutting the fibrous web 20 or the composite web 54 such that each highly bonded region 34 has an aperture 38 located completely within the highly bonded region 34 as illustrated in FIGS. 4, 5 and 6. For an aperture 38 to be "located completely within" the highly bonded region 34, the highly bonded region 34 defines a highly bonded perimeter 37, each aperture 38 defines an aperture area 39 and the aperture area 39 is located completely within the highly bonded perimeter 37 as illustrated in FIGS. 8 and 10. In various embodiments, at least 90 percent, at least 80 percent, at least 70 percent, at least 60 percent or at least 50 percent of the highly bonded regions 34 have an aperture 38 located completely within the highly bonded region 34.

In various embodiments, the method may include penetrating or cutting the fibrous web 20 or the composite web 54 such that each highly bonded region 34 has an aperture 38 concentric within the highly bonded region 34. For an aperture 38 to be "concentric within" the highly bonded region 34, the highly bonded region 34 defines a highly bonded region center point 36, each aperture 38 defines an aperture center point 40 and the aperture center point 40 is within 2 mm, in any direction, of the highly bonded region center point 36 as illustrated in FIGS. 8 and 10. In various embodiments, at least 90 percent, at least 80 percent, at least 70 percent, at least 60 percent or at least 50 percent of the highly bonded regions 34 have an aperture 38 concentric with the highly bonded region 34.

In various embodiments, the method may further include the step of heating one or more of the bonding rolls, anvil rolls, and aperture rolls. In various embodiments, the method of the present invention may include the step of removing a piece of material from the highly bonded regions 34 to create an aperture 38. In various embodiments, the method of the present invention may include bonding with a pressure bonder, a thermal bonder, an ultrasonic bonder, and the like, and combinations thereof.

In various embodiments, the method of the present invention may include aperturing with pins, water jets, needles, cutters, and the like, and combinations thereof. The aperturing step may also be accomplished by using a second bonding roll that is a thermal bonder, pressure bonder, or ultrasonic bonder. The second bonding roll may be adapted to bond completely through the one or more fibrous webs to create the apertures.

Any or all of the respective fibrous webs 20, 50, 52 and 54 of the present invention may be formed by any suitable natural or synthetic fibers in any appropriate structure, although in the embodiments shown in the accompanying drawings, these fibers are formed into nonwoven webs. In general, each nonwoven web of the present invention can be prepared from noncontinuous fibers, continuous filaments or a combination thereof. The webs may be produced by dry staple processes, or more specifically, carded web techniques, as known to those of ordinary skill in the art. Any or all of the webs of the present invention may be produced by spunbonding, meltblowing, airlaying and other techniques known to those of ordinary skill in the art that produce noncontinuous fibers and continuous filaments. Carded webs suitable for use in the practice of the present invention can have the fibers in an aligned or an unaligned configuration. Conventional carding machines, as known to those of ordinary skill in the art, can be employed in producing the respective layers of the present invention.

Commercially available thermoplastic polymeric materials can be advantageously employed in any or all of the webs of the present invention. Examples of such polymers, by way of illustration only, include polyolefins, polyamides, polyesters, and the like. The fibers may have any suitable morphology and may include hollow or core fibers, shaped fibers, bicomponent fibers or high absorbent particle impregnated fibers.

In various embodiments, the fibrous web 20 or the composite web 54 may comprise a plurality of highly bonded regions 34 wherein each highly bonded region 34 includes a single aperture 38 located therein. In various embodiments, the fibrous web 20 or the composite web 54 may comprise less bonded regions 42 wherein the one or more less bonded regions 42 are free of apertures 38 or are substantially free of apertures 38.

In various embodiments, at least 90 percent, at least 80 percent, at least 70 percent, at least 60 percent or at least 50 percent of the highly bonded regions 34 of the fibrous web 20 or the composite web 54 have an aperture 38 located at the center of the highly bonded region 34.

In various embodiments, at least 90 percent, at least 80 percent, at least 70 percent, at least 60 percent or at least 50 percent of the highly bonded regions 34 of the fibrous web 20 or the composite web 54 have an aperture 38 located completely within the highly bonded region 34.

In various embodiments, at least 90 percent, at least 80 percent, at least 70 percent, at least 60 percent or at least 50 percent of the highly bonded regions 34 of the fibrous web 20 or the composite web 54 have an aperture 38 concentric with the highly bonded region 34.

In various embodiments, the single fibrous web 20, the first fibrous web 50 and/or the second fibrous web 52 may have a density of 0.008 grams/cubic centimeter (g/cc) to 0.15 g/cc and a basis weight of 20 grams/square meter (gsm) to 120 gsm. In particular embodiments, the composite web 54 may include a first fibrous web 50 having a density of about 22 gsm and a density of about 0.06 g/cc and a second fibrous web 52 having a density of 0.017 to 0.025 g/cc and a basis weight of at least 20 gsm. In various embodiments, the single fibrous web 20, the first fibrous web 50 and/or the second fibrous web 52, may have a basis weight of at least 20 gsm, at least 30 gsm, at least 40 gsm, at least 50 gsm, at least 60 gsm, at least 70 gsm and at least 80 gsm. In various embodiments, the single fibrous web 20, the first fibrous web 50 and/or the second fibrous web 52 may have a basis weight of more than 90 gsm. In various embodiments, the single fibrous web 20, the first fibrous web 50 and/or the second fibrous web 52 may have a density of less than 0.07 g/cc, 0.06 g/cc, 0.05 g/cc, 0.04 g/cc, less than about 0.03 g/cc, less than about 0.025 g/cc, less than about 0.02 g/cc, less than about 0.015 g/cc and less than about 0.01 g/cc.

Either of the fibrous webs 20 or 54, described herein, may be suitable as end products for such uses as wipers, towels, meat tray mats, and the like. Additionally, either of the fibrous webs 20 or 54 described herein may be suitable for use as a component of a disposable absorbent article, such as a diaper.

Figure 11:
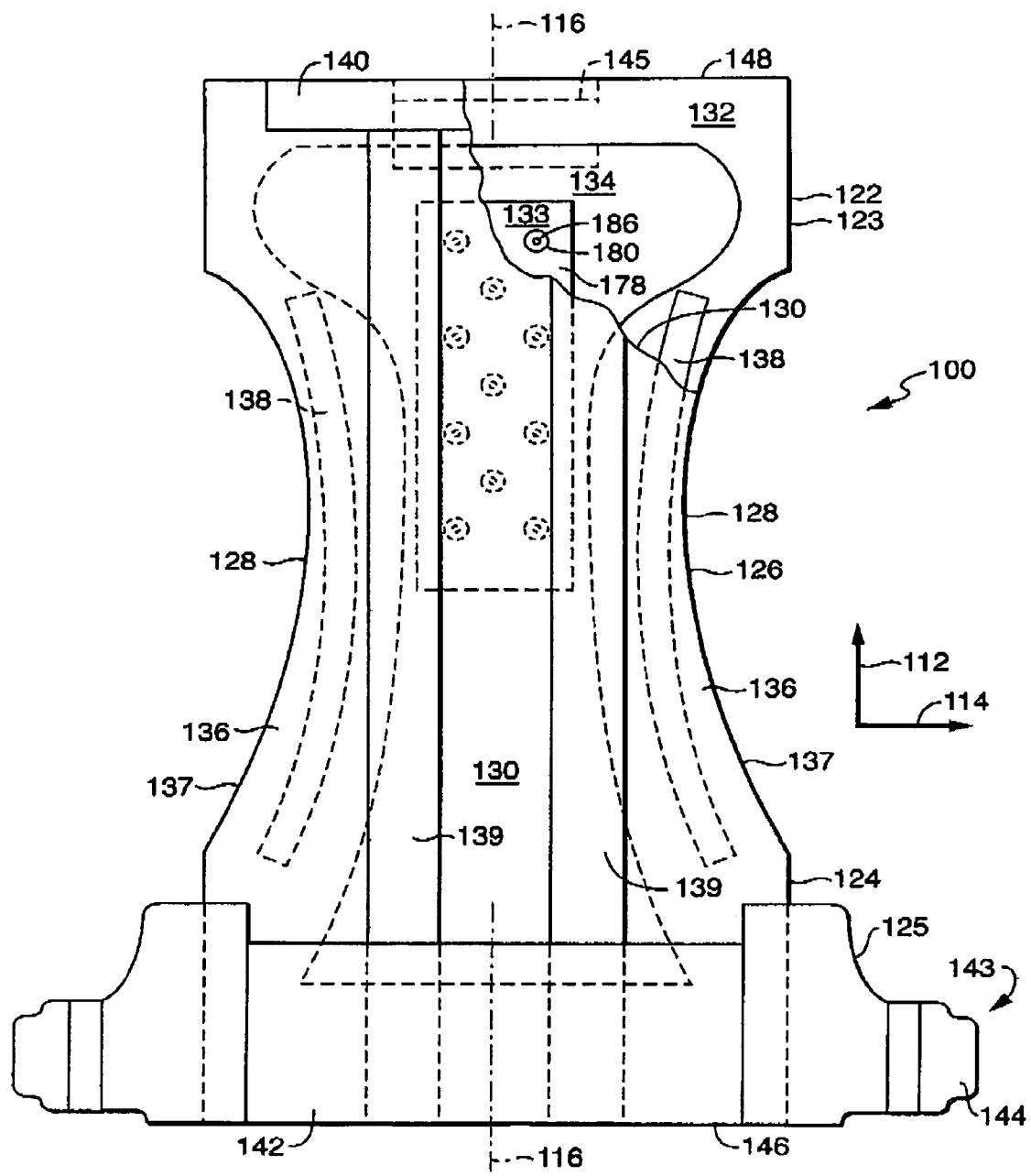
FIG. 11 representatively illustrates an exemplary diaper including an exemplary material made according to the present method and apparatus.

FIG. 11 representatively illustrates a diaper 100 of the present invention in an unfastened condition with the surface of the diaper which contacts the wearer facing the viewer. Portions of the diaper 100 have been cut away to illustrate underlying structure. The diaper 100 has a longitudinal direction 112 and a lateral direction 114. The diaper 100 has a longitudinal centerline 116 depicted as a dashed line.

The diaper 100, in the longitudinal direction 112, defines a front portion 122, a back portion 124, and a crotch portion 126 connecting the front portion 122 and the back portion 124. The diaper 100 includes a bodyside liner 130, an outer cover 132 and an absorbent core 134 located between the bodyside liner 130 and the outer cover 132. The diaper 100 may also include a surge portion 133 joined to the absorbent core 134 and/or the bodyside liner 130. Alternatively, the surge portions 133 may not be joined to either the absorbent core 134 or the bodyside liner 130. The front portion 122 may include, at least partially, one or more front ears 123. The back portion 124 may include, at least partially, one or more back ears 125. The front ears 123 and/or the back ears 125 may be formed from extensions of the bodyside liner 130, the outer cover 132, combinations of both the bodyside liner 130 and the outer cover 132, or by the addition of one or more separate components as is known in the art. The front portion 122 has a front waist edge 148 and the back portion 124 has a back waist edge 146.

The diaper 100 also includes a fastener system 143. The fastener system 143 includes one or more back fasteners 144 and one or more front fasteners 145. Portions of the fastener system 143 may be included in the front portion 122, back portion 124, or both. The fastener system 143 is adapted to secure the diaper 100 about the waist of a wearer and maintain the diaper 100 in place during use.

As used herein, reference to a front portion refers to that part of the diaper which is generally located on the front of a wearer when in use. Reference to the back portion refers to the portion of the diaper generally located at the back of the wearer when in use, and reference to the crotch portion refers to that portion which is generally located between the legs of the wearer when in use.

The crotch portion 126 has opposite longitudinal side portions 128 which may include a pair of elasticized, longitudinally-extending leg cuffs 136. The leg cuffs 136 are generally adapted to fit about the legs of a wearer in use and serve as a mechanical barrier to the lateral flow of body exudates. The leg cuffs 136 may be elasticized by a pair of leg elastics 138. The diaper 100 may further include a front waist elastic 140 and/or a back waist elastic 142.

The bodyside liner 130 of the absorbent article 100, as representatively illustrated in FIG. 11, suitably presents a body-facing surface which is compliant, soft feeling, and non-irritating to the wearer's skin. Further, the bodyside liner 130 may be less hydrophilic than the absorbent core 134, to present a relatively dry surface to the wearer, and may be sufficiently porous to be liquid permeable, permitting liquid to readily penetrate through its thickness. A suitable bodyside liner 130 may be manufactured from a wide selection of web materials such as porous foams, reticulated foams, apertured plastic films, natural fibers (for example, wood or cotton fibers), synthetic fibers (for example, polyester or polypropylene fibers), or a combination of natural and synthetic fibers. The bodyside liner 130 is suitably employed to help isolate the wearer's skin from liquids held in the absorbent core 134.

Various woven and nonwoven fabrics can be used for the bodyside liner 130. For example, the bodyside liner may be composed of a meltblown or spunbonded web of polyolefin fibers. The bodyside liner 130 may also be a bonded carded web composed of natural and/or synthetic fibers. The bodyside liner 130 may be composed of a substantially hydrophobic material, and the hydrophobic material may, optionally, be treated with a surfactant or otherwise processed to impart a desired level of wettability and hydrophilicity. In a particular aspect of the present invention, the bodyside liner 130 comprises a nonwoven, spunbond, polypropylene fabric composed of about 2.8 to 3.2 denier fibers formed into a web having a basis weight of about 22 grams per square meter and a density of about 0.06 grams per cubic centimeter. The fabric is surface treated with about 0.28 weight percent of a surfactant commercially available from Rohm and Haas Company under the trade designation Triton X-102. The surfactant can be applied by any conventional means, such as spraying, printing, brush coating, and the like.

The outer cover 132 of the diaper 100 suitably presents a garment facing surface which is intended to be worn adjacent the clothing of the wearer. The outer cover 132 may be a polyethylene film. Alternative constructions of the outer cover 132 may comprise a woven or nonwoven fibrous web layer which has been totally or partially constructed or treated to impart a desired level of liquid impermeability to selected regions of the backsheet that are adjacent or proximate the absorbent core 134. For example, a clothlike backsheet may be composed of polypropylene spunbond fabric which is laminated and thermally bonded to a stretch-thinned polypropylene film. Outer cover 132 may optionally include a micro-porous, "breathable" material which permits vapors to escape from diaper 100 while still preventing liquid exudates from passing through. For example, the outer cover 132 may be composed of a microporous polymer film or a nonwoven fabric which has been coated or otherwise treated to impart a desired level of liquid impermeability. The outer cover 132 can also be embossed or otherwise provided with a matte finish to exhibit a more aesthetically pleasing appearance. The size of outer cover 132 is typically determined by the size of diaper 100 and the exact diaper design selected.

The bodyside liner 130 and outer cover 132 are generally joined in facing relationship with the absorbent core 134 located therebetween. The bodyside liner 130 and the outer cover 132 may be joined to each other around the outer periphery of the diaper 100 by any means known to those skilled in the art such as adhesive bonds, sonic bonds, thermal bonds, and the like, and combinations thereof. As used herein, the term "join", and derivatives thereof, encompass configurations wherein an element is directly secured to the other element by affixing the element directly to the other element, and configurations wherein the element is indirectly secured to the other element by affixing the element to intermediate member(s) which in turn are affixed to the other element.

The leg cuffs 136 are suitably formed by portions of the outer cover 132 and/or bodyside liner 130, which extend beyond the longitudinal sides of the absorbent core 134. Alternatively, the leg cuffs 136 can be formed from separate materials joined to the outer cover 132 and/or bodyside liner 130. In some embodiments, the leg cuffs 136 may have an arcuate shape resulting from a leg cut out 137. In other embodiments, the leg cuffs 136 may have a generally straight leg cut out 137.

The leg elastics 138, front waist elastics 140, back waist elastics 142, and other elastic materials may also be provided to draw and hold the diaper 100 against the legs and/or waist of the infant to improve gasketing and minimize leakage. Materials suitable for use in forming the leg elastics 138 and/or the waist elastics 140 and 142 are known to those skilled in the art. Exemplary of such materials are strands or ribbons of a polymeric, elastomeric material which are adhered to the diaper 100 in a stretched position, or which are joined to the diaper while the diaper is pleated, such that elastic constrictive forces are imparted to the diaper 100. The leg elastics 138 and waist elastics 140 and 142 may have any configuration which provides the desired performance. The leg elastics 138 may be generally straight or optionally curved to more closely fit the contours of the legs and buttocks of the wearer and better contain bodily exudates. The leg elastics 138 and waist elastics 140 and 142 may be joined to the diaper 100 in any of several ways which are well known to those skilled in the art. For example, the elastics may be joined to the diaper 100 by ultrasonic bonding, thermal bonding, adhesive bonding, and the like, and combinations thereof.

The front ears 123 and/or the back ears 125 are suitably formed by portions of the outer cover 132, and/or bodyside liner 130, which extend beyond the longitudinal sides of the absorbent core 134. Alternatively, the front ears 123 and/or back ears 125 may be formed from separate materials which are joined to the outer cover 132 and/or bodyside liner 130.

The fastener system 143 provides a means for securing the diaper 100 on the wearer. The fastener system 143 includes at least one back fastener 144 and at least one front fastener 145. In some embodiments, the fastener system 143 includes two back fasteners 144 and one front fastener 145.

In some embodiments, the back fasteners 144 may be joined to the back portion 124, the back ears 125 or both and the front fasteners 145 may be joined to the front portion 122, the front ears 123, or both. The back fasteners 144 may be one or more discrete pieces of material joined to the diaper 100 and adapted to align with and work in conjunction with the front fasteners 145, which may be one or more discrete pieces of material joined to the diaper 100. For example, the front fastener 145 may be a piece of loop material joined with the outercover 132 in the front portion 122 and configured to engage hook-type back fasteners 144 when the diaper 100 is wrapped about the waist and legs of a user.

The absorbent core 134 is positioned between the bodyside liner 130 and the outer cover 132 to form the diaper 100. The absorbent core 134 is generally conformable and capable of absorbing and retaining body exudates. The absorbent core 134 may include superabsorbent material, staple fibers, binder fibers, and the like, and combinations thereof, as is known in the art. The absorbent core 134 may have any of a number of shapes and sizes. For example, the composite absorbent core may be rectangular, I-shaped or T-shaped. The size and absorbent capacity of the absorbent core 134 should be compatible with the size of the intended wearer and the fluid loading imparted by the intended use of the diaper.

Containment flaps 139 may be connected to the bodyside liner 130 or other components as is well known in the art. Suitable configurations of the containment flaps are described, for example, in U.S. Pat. No. 5,599,338 issued Feb. 4, 1997, to K. Enloe, the entirety of which is incorporated herein by reference where not contradictory.

In various embodiments, the surge portion 133 serves to quickly collect and temporarily hold discharged fluids and then to eventually release the fluids into the absorbent core 134. Various woven and nonwoven fabrics can be used to construct surge management portion 133. For example, the surge management portion 133 may be a layer composed of a meltblown or spunbonded web of polyolefin fibers. The surge management layer 133 may also be a bonded carded web or an airlaid web composed of natural and synthetic fibers. The bonded carded web may, for example, be a powder bonded carded web, an infrared bonded carded web, or a through air bonded carded web. The infrared and through air bonded carded webs can optionally include a mixture of different fibers, and the fiber lengths within a selected fabric web may be within the range of about 1.0 to 3.0 inch. The surge management portion 133 may be composed of a substantially hydrophobic material, and the hydrophobic material may optionally be treated with a surfactant or otherwise processed to impart a desired level of wettability and hydrophilicity.

Surge management portion 133 can have a generally uniform thickness and cross sectional area. Alternatively, a configuration can be used wherein the bodyside surface area of the surge management portion is greater or less than the surface area of a section taken along an X-Y plane located below the bodyside surface of the surge management portion.

In various embodiments, the surge management portion 133 may be operably connected to the topsheet layer with a conventional pattern of adhesive, such as a swirl adhesive pattern. In addition, the surge management portion 133 can be operably connected to the absorbent core 134 or one or more wrapsheets covering or surrounding the absorbent core 134 with a conventional pattern of adhesive. The amount of adhesive add-on should be sufficient to provide the desired levels of bonding, but should be low enough to avoid excessively restricting the movement of liquid from the topsheet layer, through the surge management portion and through the wrapsheet layer.

Alternatively, the surge management portion 133 may be operably bonded to the topsheet layer by means of the apparatus and method of the present invention. In specific embodiments, the bodyside liner 130 and the surge portion 133 may be the first and second fibrous webs 50 and 52 respectively as discussed herein.

The surge management portion 133 can be of any desired shape consistent with the absorbency requirements of absorbent core 134. Suitable shapes include for example, circular, rectangular, triangular, trapezoidal, oblong, dog-boned, hourglass-shaped, or oval. Preferred shapes of the surge management portion 133 are those that increase the contacting, liquid communicating surface area between the surge management portion 133 and the absorbent core 134 so that the relative capillarity difference between the portions can be fully utilized. In certain embodiments, for example, the surge management portion can be generally rectangular-shaped.

In particular aspects of the invention, the fibrous nonwoven web comprising surge management portion 133 can be a bonded, uniformly mixed, single layer structure having a basis weight of at least 20 grams per square meter, a void volume between about 40 and 60 cubic centimeters per gram of web at a pressure of 689 dynes per square meter (0.01 psi), a permeability of about 5,000 to about 8,000 darcy, a porosity of about 97.2 percent to about 98.8 percent and a surface area per void volume of about 24 to about 49 square centimeters per cubic centimeters. The web fibers may be thermoplastic, and may be heat bonded to one another. In addition, the web structure can have a density within a range of about 0.017 to 0.025 gm/cc, as determined at a pressure of 689 dynes per square meter (0.01 psi).

For example, the surge management portion 133 may include a substantially homogeneous single-layer fibrous nonwoven web having a basis weight of about 48.8 gsm created by using about 40 percent by weight of a Hoechst Celanese type 295 6.0 denier polyester fibers and 60 percent by weight of a BASF 3.0 denier polyethylene sheath/polyester core bicomponent fibers. The homogeneous blend of fibers may be bonded together using hot air passed through the web mass at a temperature of 135 degree C. for approximately four seconds.

In other aspects of the invention, the fibrous nonwoven web may be made from or include a plurality of fibers bonded to one another to form a lofty nonwoven web having a basis weight of at least 20 grams per square meter. In more refined embodiments the basis weight can range from about 40 to about 68 grams per square meter. The web can be made entirely from bicomponent fibers which are typically crimped and which will generally have a fiber denier equal to or greater than 2.0 denier. Alternatively, the web can be made from a combination of fibers such as bicomponent fibers and polyester fibers. In such embodiments, the web will usually include at least 50 percent by weight of bicomponent fibers. The resultant web will have a void volume of between about 80 and about 117 cubic centimeters per gram of web at 689 dynes per square centimeter pressure, a permeability of about 8,000 to about 15,000 darcy, a porosity of about 98.6 to about 99.4 percent, a surface area per void volume of about 10 to about 25 square centimeters per cubic centimeter, a saturation capacity between about 55 and about 80 grams of 0.9 percent saline solution per gram of web and a compression resilience in both the wet and dry state of at least 60 percent. In addition, the web structure can have a density within a range of about 0.008 to 0.013 gm/cc, as determined at a pressure of 689 dynes per square meter (0.01 psi).

For example, the surge management portion may include a single layer fibrous nonwoven web having a basis weight of about 49.8 gsm created by using a uniform mixture of 40 percent by weight of a Hoechst Celanese type 224, 6.0 denier polyester staple fibers and 60 percent by weight of a Chisso-type ES P, 3.0 denier by 38 millimeter polypropylene sheath/polypropylene core bicomponent fiber. The web may be bonded using hot air at a temperature of 135 degree C. for approximately four seconds. The resultant web may exhibit a void volume of about 84 cc/gm, a SA/VV (surface area per void volume) value of about 20 $cm^2/cc$, a porosity of about 98.9 percent, a permeability of about 9256 darcy, a saturation capacity of about 59 gm/gm, a wet compression resilience of about 76 percent, and a dry compression resilience of about 76 percent.

As another example, a substantially homogeneous single-layer fibrous nonwoven web having a basis weight of 51.9 gsm may be created by using 20 percent by weight of a Hoechst Celanese type 295, 6.0 denier polyester fibers; 20 percent by weight of a Hoechst Celanese type 183, 1.5 denier polyester fibers and 60 percent by weight of a BASF 3.0 denier polyethylene sheath/polyester core bicomponent fibers. The homogeneous blend of fibers may be bonded together using hot air at a temperature of 135 degree C. for approximately four seconds. The resultant web may exhibit a void volume of about 110 cc/gm, a SA/VV value of about 16.2 $cm^2/cc$, a porosity of about 99.3 percent, a permeability of about 13,189 darcy, a saturation capacity of about 79 gm/gm, a wet compression resilience of about 73 percent, and a dry compression resilience of about 70 percent.

It will be readily apparent that absorbent articles requiring more surge capacity may also require proportionally greater amounts of surge management material. The surge management material, however, need not be of uniform basis weight throughout its areal extent, but instead can be arranged so that some sections have more surge management material compared to other sections. For the purposes of the present invention, the effective basis weight will be the weight of the surge management material divided by the area over which the surge management portion extends. The surge management material employed with the present invention will be at least about 20 grams per square meter with no real upper limit, with the target range being from about 40 to about 68 grams per square meter.

Suitable surge materials are described in U.S. Pat. No. 5,522,810 issued Jun. 4, 1996 to Allen, Jr. et al. and U.S. Pat. No. 5,562,650 issued Oct. 8, 1996 to Everett et al., the entireties of both are incorporated herein by reference where not contradictory.

As illustrated in FIG. 11, the surge portion 133 has a plurality of highly bonded regions 180 surrounded by a less bonded region 178. The plurality of highly bonded regions 180 each include one aperture 186 located within the highly bonded region 180. The highly bonded regions 180, less bonded region 178 and apertures 186 may be created using the method and apparatus described herein.

Figure 12:
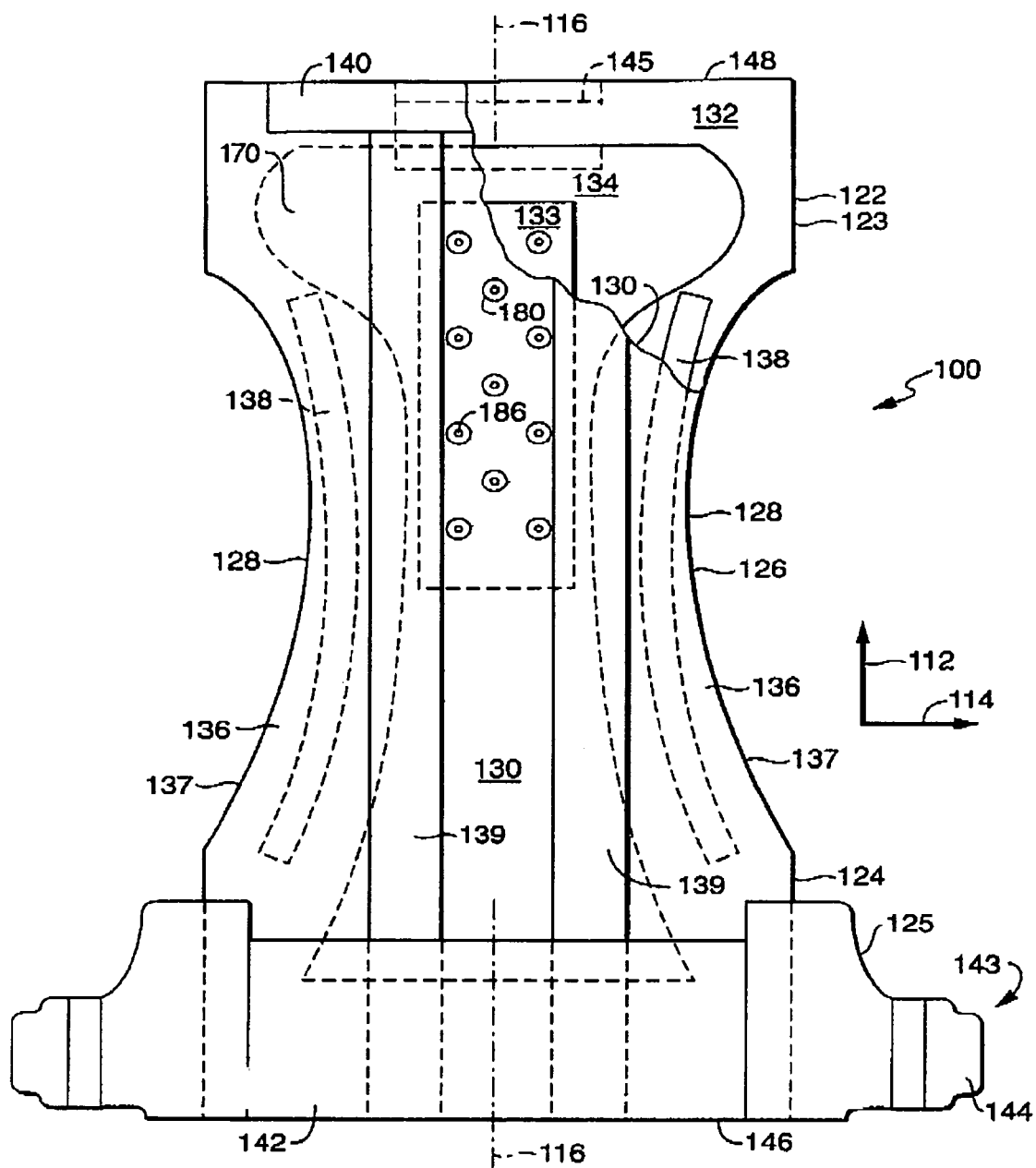
FIG. 12 representatively illustrates an exemplary diaper including an exemplary material made according to the present method and apparatus.

Referring now to FIG. 12, a diaper 100 includes a bodyside composite 170. The bodyside composite 170 includes a bodyside liner 130 bonded to a surge portion 133 at a plurality of highly bonded regions 180. Each highly bonded region 180 contains one aperture 186 located within the highly bonded region 180. The highly bonded regions 180, less bonded region 178 and apertures 186 may be created using the method and apparatus described herein.

In various embodiments, the surge material 133 or the bodyside composite 170 may comprise a plurality of highly bonded regions 180 wherein one or more of the highly bonded regions 180 includes a single aperture 186 located therein.

In various embodiments, the surge material 133 or the bodyside composite 170 may comprise low bonded regions 178 wherein the one or more less bonded regions 178 are free of apertures 186 or are substantially free of apertures 186.

In various embodiments, the surge material 133 or the bodyside composite 170 may comprise a plurality of highly bonded regions 180 wherein each highly bonded region 180 has an aperture 186 located at the center of the highly bonded region 180. For an aperture 186 to be located at the center of the highly bonded region 180, the highly bonded region 180 defines a center point 181, each aperture 186 defines an aperture area 187 and the highly bonded region center point 181 is located within the aperture area 187. In various embodiments, at least 90 percent, at least 80 percent, at least 70 percent, at least 60 percent or at least 50 percent of the highly bonded regions 180 have an aperture 186 located at the center point 181 of the highly bonded region 180. In various embodiments, one or more highly bonded regions may have a single aperture 186 located at the center.

In various embodiments, the surge material 133 or the bodyside composite 170 may comprise a plurality of highly bonded regions 180 wherein each highly bonded region 180 has an aperture 186 located completely within the highly bonded region 180. For an aperture 186 to be located completely within the highly bonded region 180, the highly bonded region 180 defines a highly bonded perimeter 182, each aperture 186 defines an aperture area 187 and the aperture area 187 is located completely within the highly bonded perimeter 182. In various embodiments, at least 90 percent, at least 80 percent, at least 70 percent, at least 60 percent or at least 50 percent of the highly bonded regions 180 have an aperture 186 located completely within the highly bonded region 180. In various embodiments, one or more highly bonded regions may have a single aperture 186 located completely within the highly bonded region.

In various embodiments, the surge material 133 or the bodyside composite 170 may comprise a plurality of highly bonded regions 180 wherein each highly bonded region 180 has an aperture 186 concentric with the highly bonded region 180. For an aperture 186 to be concentric with the highly bonded region 180, the highly bonded region 180 defines a highly bonded region center point 181, each aperture 186 defines an aperture center point 188 and the aperture center point 188 is within 2 mm, in any direction, of the highly bonded region center point 181. In various embodiments, at least 90 percent, at least 80 percent, at least 70 percent, at least 60 percent or at least 50 percent of the highly bonded regions 180 have an aperture 186 concentric with the highly bonded region 180. In various embodiments, one or more highly bonded regions may have a single aperture 186 concentric with the highly bonded region 180.

Accordingly, while this invention has been described by reference to the above embodiments and examples, it will be understood that this invention is capable of further modifications. This application is, therefore, intended to cover any variations, uses or adaptations of the invention following the general principles thereof, and including such departures from the present disclosure as come within known or customary practice in the art to which this invention pertains and fall within the limits of the appended claims.

The invention claimed is:

1. A method of aperturing a fibrous web comprising:
   a. providing a fibrous web comprising at least partially unbonded fibers;
   b. moving the fibrous web through a bonding nip created by a rotatable bonding roll and a rotatable anvil roll, the rotatable bonding roll having a peripheral bonding surface and a plurality of protuberances extending from the peripheral bonding surface, the plurality of protuberances defining a bonding pattern;
   c. bonding the fibrous web with the plurality of protuberances at a plurality of highly bonded regions, the plurality of highly bonded regions being surrounded by at least one less bonded region, the at least partially unbonded fibers being plasticized at the plurality of highly bonded regions;
   d. maintaining the at least partially unbonded fibers of the fibrous web at the at least one less bonded region;
   e. moving the fibrous web with the plurality of highly bonded regions through an aperture nip created by a rotatable aperture roll and the rotatable anvil roll, the rotatable aperture roll having a peripheral aperture surface and a plurality of projections extending from the peripheral aperture surface, the plurality of projections defining an aperturing pattern, the aperturing pattern substantially aligning with the bonding pattern; and
   f. aperturing the fibrous web at the plurality of highly bonded regions with the plurality of projections creating apertures within at least 50 percent of the highly bonded regions.

2. The method of claim 1 wherein the fibrous web has a density of less than 0.025 g/cc and a basis weight of at least 40 gsm.

3. The method of claim 1 wherein the bonding roll is a pressure bonder, thermal bonder or ultrasonic bonder.

4. The method of claim 1 wherein each apertured highly bonded region includes a single aperture located therein.

5. The method of claim 1 wherein each apertured highly bonded region defines a center and has an aperture located at the center.

6. The method of claim 5 wherein the apertures are located completely within the highly bonded regions.

7. The method of claim 6 wherein the less bonded region is substantially free of apertures.

8. A method of bonding and aperturing fibrous webs comprising:
   a. providing first and second fibrous webs;
   b. moving the first and the second fibrous webs in facing relation through a bonding nip created by a rotatable bonding roll and a rotatable anvil roll, the rotatable bonding roll having a peripheral bonding surface and a plurality of protuberances extending from the peripheral bonding surface, the plurality of protuberances defining a bonding pattern;
   c. bonding the first and second fibrous webs together in the bonding nip to create a composite web, the bonding occurring at least at a plurality of highly bonded regions, the plurality of highly bonded regions being surrounded by at least one less bonded region;
   d. moving the composite web through a second nip created by a rotatable aperture roll and the rotatable anvil roll, the rotatable aperture roll having a peripheral aperture surface and a plurality of projections extending from the peripheral aperture surface, the plurality of projections defining an aperturing pattern, the aperturing pattern substantially aligning with the bonding pattern; and
   e. aperturing the composite web at the plurality of highly bonded regions with the plurality of projections creating apertures within at least 50 percent of the highly bonded regions.

9. The method of claim 8 wherein the first fibrous web has a density of at least 0.05 g/cc and a basis weight of less than 25 gsm and the second fibrous web has a density of less than 0.025 g/cc and a basis weight of at least 40 gsm.

10. The method of claim 8 wherein the contact roll is a pressure bonder, thermal bonder or ultrasonic bonder.

11. The method of claim 8 wherein each apertured highly bonded region includes a single aperture located therein.

12. The method of claim 8 wherein each apertured highly bonded region defines a center and has an aperture located at the center.

13. The method of claim 12 wherein the apertures are located completely within the highly bonded regions.

14. The method of claim 13 wherein the less bonded region is substantially free of apertures.

15. The method of claim 8 wherein the aperturing step further includes removing a portion of the composite web at one or more of the highly bonded regions to create one or more of the apertures.

* * * * *